(12) United States Patent
Casey et al.

(10) Patent No.: US 8,473,221 B2
(45) Date of Patent: Jun. 25, 2013

(54) PROCESS, SOFTWARE ARRANGEMENT AND COMPUTER-ACCESSIBLE MEDIUM FOR OBTAINING INFORMATION ASSOCIATED WITH A HAPLOTYPE

(75) Inventors: Will Casey, Columbia, MT (US); Tom Anantharaman, DeForest, WI (US); Bhubaneswar (Bud) Mishra, Great Neck, NY (US)

(73) Assignees: New York University, New York, NY (US); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/890,464

(22) Filed: Sep. 24, 2010

(65) Prior Publication Data

US 2011/0087437 A1    Apr. 14, 2011

Related U.S. Application Data

(63) Continuation of application No. 11/093,565, filed on Mar. 30, 2005, now Pat. No. 7,805,282.

(60) Provisional application No. 60/557,768, filed on Mar. 30, 2004.

(51) Int. Cl.
*G06F 19/00* (2011.01)
*G06F 15/00* (2006.01)
*G11C 17/00* (2006.01)
*C12Q 1/68* (2006.01)

(52) U.S. Cl.
USPC ............... 702/20; 365/94; 700/1; 435/6.1

(58) Field of Classification Search
None
See application file for complete search history.

(56) References Cited

U.S. PATENT DOCUMENTS

| | | | |
|---|---|---|---|
| 5,866,404 | A | 2/1999 | Bradshaw et al. |
| 7,286,941 | B1 * | 10/2007 | Thomas .......................... 702/19 |
| 2003/0059808 | A1 | 3/2003 | Liu et al. |
| 2003/0170665 | A1 | 9/2003 | Daly et al. |
| 2003/0171878 | A1 | 9/2003 | Frudakis |
| 2003/0195707 | A1 | 10/2003 | Schork et al. |
| 2004/0224331 | A1 | 11/2004 | Cantor et al. |
| 2004/0267458 | A1 | 12/2004 | Judson et al. |
| 2005/0037393 | A1 | 2/2005 | Gunderson et al. |
| 2006/0234221 | A1 * | 10/2006 | Cohen et al. ..................... 435/6 |

OTHER PUBLICATIONS

Anantharaman et al. "Fast and Cheap Genome Wide Haplotype Construction Via Optical Mapping", 2005, Pacific Symposium on Biocomputing, vol. 10, pp. 385-396.*
Casey, Will et al., "A Nearly Linear-Time General Algorithm for Genome-Wide Bi-allele Haplotype Phasing", 2003, *High Performance Computing* vol. 2913, pp. 204-215.
Excoffier, Laurent et al., "Maximum-Likelihood Estimation of Molecular Haplotype Frequencies in a Diploid Population", *Molecular Biology and Evolution*, 1995, vol. 12, No. 4, pp. 921-927.
Niu, Tianhua et al., "Bayesian Haplotype Inference for Multiple Linked Single-Nucleotide Polymorphisms", 2002, *American Journal of Human Genetics*, vol. 70, pp. 157-169.
Ruano, G. et al., "Haplotype of Multiple Polymorphisms Resolved by Enzymatic Amplification of Single DNA Molecules", *Proc. Natl. Acad. Sci. USA*, vol. 87, pp. 6296-6300, Aug. 1990.
Tsutsumi, et al., "Manno-Sebinding Lectin Gene: Polymorphisms in Japanese Patients with Systemic Lupus Erthematosus, Rheumatoid Arthritis and Sjogren's Syndrome", *Genes and Immunity*, 2001, vol. 2, pp. 99-104.
International Search Report and Written Opinion for International Application No. PCT/US05/10664 mailed Dec. 18, 2006.
W. Casey "Graph Embeddings with Applications in Genomic Experiments," ProQuest, Aug. 9, 2002.
Will Casey et al., "A Nearly Linear-Time General Algorithm for Genome-Wide Bi-allele Haplotype Phasing" T.M. Pinkston and V.K. Prasanna (Eds.):HiPC2003, LNCS2913, pp. 204-215.
T. Anantharaman et al., "Fast & Cheap Genome Wide Haplotype Construction Via Optical Mapping" NYU Technical Report #TR2004-852, Jun. 7, 2004.

* cited by examiner

*Primary Examiner* — John S Brusca
(74) *Attorney, Agent, or Firm* — Dorsey & Whitney LLP

(57) ABSTRACT

The present invention relates to a method, system and software arrangement for determining the co-associations of allele types across consecutive loci and hence for reconstructing two haplotypes of a diploid individual from genotype data generated by mapping experiments with single molecules, families or populations. The haplotype reconstruction system, method and software arrangement of the present invention can utilize a procedure that is nearly linear in the number of polymorphic markers examined, and is therefore quicker, more accurate, and more efficient than other population-based approaches. The system, method, and software arrangement of the present invention may be useful to assist with the diagnosis and treatment of any disease, which has a genetic component.

24 Claims, 5 Drawing Sheets

PROCESS, SOFTWARE ARRANGEMENT AND COMPUTER-ACCESSIBLE MEDIUM FOR OBTAINING INFORMATION ASSOCIATED WITH A HAPLOTYPE

CROSS REFERENCE TO RELATED APPLICATION(S)

The present application is a continuation of U.S. patent application Ser. No. 11/093,565, filed Mar. 30, 2005, now U.S. Pat. No. 7,805,282, entitled "Process, Software Arrangement and Computer-Accessible Medium for Obtaining Information Associated with a Haplotype" (the "'565 Application") and claims priority therefrom pursuant to 35 U.S.C. §§120 and 121. The present application also claims priority from U.S. Patent Application Ser. No. 60/557,768, filed Mar. 30, 2004, entitled "System, Method and Software Arrangement for Bi-allele Haplotype Phasing" (the "'768 Application") pursuant 35 U.S.C. §§119(e) and 120. The entire disclosures of both the '565 Application and the '768 Application are hereby incorporated herein by reference.

BACKGROUND OF THE INVENTION

1. Field of the Invention

The present invention relates to a system, method, and software arrangement for determining co-associations of allele types across consecutive genetic loci, permitting the haplotyping of genetic samples at one or more contiguous loci. The system, method, and software arrangement described herein can employ genotype data generated from a wide range of mapping methods to determine chromosomal haplotypes. As such, the system, method, and software arrangement of the present invention may be useful as an aid to the diagnosis and treatment of any disease which has a genetic component.

2. Background Information

Diploid organisms are those whose somatic cells contain two copies of each chromosome. Each of these two copies of a particular chromosome may be distinguished by the presence, within the DNA which comprises the chromosome, of certain genetic variations, which may include restriction fragment length polymorphisms (RFLPs), single nucleotide polymorphisms (SNPs), sequence tag sites (STSs), microinsertions, microdeletions, or variable numbers of tandemly repeated elements (VNTRs). Based on the presence or absence of particular polymorphisms at specific loci, chromosomes may be assigned to one of two "haplotypes," the name used to refer to the collection of identifiable genetic features present on one of the two haploid chromosomes that are contained within the diploid set. In certain situations, particular haplotypes may be associated with the presence or absence of a particular mutation or other functional variation in specific genetic loci. Because these genetic variations or genotypes may be associated with certain disease states or even with predisposition to disease, determination of relationships between haplotypes and genotypes are of intense interest in genetic research.

One of the most difficult problems in determining haplotypes in diploid organisms is establishing the proper assignment of multiple polymorphic markers to the same chromosome. Thus, distribution of two different variants (or alleles) at two different genetic loci, for example A/a and B/b, could generate haplotypes AB, Ab, aB or ab depending upon the distribution of the two alleles between the two chromosomes. The problems of inferring diploid haplotypes through the use of population data have been extensively investigated and widely acknowledged. See Clark, 1990, Mol. Biol. Evol. 7:111-122; Excoffier and Slatkin, 1995, Mol. Biol. Evol. 12:921-927; Ma et al. 2000, Neural Computation 12:2881-2907; Gusfield, 2001, J. Computational Biology 8:305-323; Stephens et al., 2001, Am. J. Hum. Genet. 68:978-989; and Niu et al., 2002, Am. J. Hum. Genet. 70:156-169.

SUMMARY OF THE INVENTION

The present invention relates to a system, method, and software arrangement for determining co-associations of allele types across consecutive genetic loci, permitting the haplotyping of genetic samples at one or more contiguous loci. The system, method, and software arrangement described herein can employ genotype data generated from a wide range of mapping methods to determine chromosomal haplotypes. According to one exemplary embodiment of the present invention the system, method, and software arrangement for haplotype reconstruction of the instant invention detects polymorphic marker types at one or more contiguous genetic loci and then establishes the maximum likelihood that an arbitrary assignment of polymorphic markers to a particular haplotype adequately account for the particular genotypes observed at any given locus. The system, method, and software arrangement described herein may be useful as an aid to the diagnosis and treatment of any disease that has a genetic component associate therewith.

In contrast to these previous approaches, the present invention addresses the use of multiple independent mapping techniques (for example, those performed on a collection of large DNA fragments) as a source of the base data used to infer haplotypes. Such single molecule methods and technologies, which include optical mapping and "polony" (See Mitra et al., 1999, "In Situ Localized Amplification and Contact Replication of Many Individual DNA Molecules," *Nucleic Acids Research* 27:e34-e34), may permit the application of high-throughput methodologies to the haplotyping of a diploid individual in a population. Moreover, unlike the previous haplotyping approaches described above, the present invention determines the haplotype of an individual without reliance upon the haplotype statistics of the population to which the individual belongs. A further advantage of the instant method is its potential to determine an individual's haplotype with accuracy and resolution far beyond methods based on population studies, both in the worst-case and in the average-case scenarios.

Thus, in accordance with an exemplary embodiment of the present invention, a system, process and software arrangement are provided for obtaining information associated with a haplotype of one or more genetic samples from genotype data. In particular, the genotype data is received, and polymorphic genetic markers are identified from the genotype data. Further, at least one association of the polymorphic genetic markers across genetic loci (which can be consecutive) may be determined to obtain the information.

In one further embodiment of the present invention, the genotype data can be obtained from the corresponding one or more genetic samples, the genotype data being contained in at least one dataset. The association can be determined at one or more contiguous loci. The determined association may constitute the haplotype of the one or more genetic samples. The polymorphic genetic markers may be restriction fragment length polymorphisms ("RFLPs"), single nucleotide polymorphisms ("SNPs"), sequence tag sites ("STSs"), insertions, microinsertions, deletions, microdeletions, variable numbers of tandemly repeated elements ("VNTRs"), microsatellites, expanded repeats of variable repeat number, or any combination thereof.

In still another exemplary embodiment of the present invention, the genotype data can be obtained from single DNA molecules with locations of polymorphic genetic markers. The polymorphic genetic markers are determined using at least one of a Maximum Likelihood Estimator ("MLE") algorithm and an Expectation Maximization ("EM") algorithm. The polymorphic genetic markers may be defined as events, and $$X(D) = \begin{cases} 1 & \text{if } \hat{\Phi}(D): |\hat{\mu}_1 - \hat{\mu}_2| - \delta > 0 \\ 0 & o.w., \end{cases}$$

where $\hat{\Phi}(D)$ denotes the limit of the EM-algorithm with data set D at the loci j.

For example, the associations of the polymorphic genetic markers across consecutive genetic loci at one or more contiguous loci are determined through the formulation of a maximum likelihood problem. The likelihood function of the maximum likelihood problem can be given by:

$$L(\theta) = P(D \mid \theta) = \frac{\Gamma(N)}{\prod_{\rho \in M} \Gamma(N\alpha_\rho)} \prod_{\rho \in M} \theta_\rho^{\alpha_\rho N},$$

and the maximum likelihood estimation can include a finding $\rho \in A$ so that $L(\rho) \geq L(\omega) \forall \omega \in A$.

For a set of genetic loci $\{j_1, j_2, \ldots, j_\nu\}$, a likelihood function $L_{M[j_1, j_2, \ldots, j_\nu]}$ can be defined as that most likely to produce posterior $\alpha_{j_1, j_2, \ldots, j_\nu}$ over the space $M[j_1, j_2, \ldots, j_\nu]$. The associations of the polymorphic genetic markers across the genetic loci at one or more contiguous loci are determined through maximizing $\Pi_{\rho \in \{C^1_1\}^{M-1}} \theta_\rho^{\alpha_\rho N}$ over $\theta \in$ or minimizing $$\sum_{j \in (1 \ldots M)} \frac{(\alpha_j - \theta_j)^2}{\alpha_j}$$

over $\theta \in A$.

The associations of the polymorphic genetic markers at one or more loci, thereby producing a contig, can be determined through an application of a VERIFY-PHASE function. The VERIFY-PHASE function may determine one or more selected phasing criteria. The phasing criteria may be a statistically-significant rejection of Hardy-Weinberg Equilibrium. The association of the polymorphic genetic markers over the contig can be computed through application of a MLE-COLLAPSE function. Further, the association of polymorphic genetic markers at one or more contiguous loci, thereby producing a contig, can be determined through an application of a COMPUTE-PHASE function or a JOIN function.

According to yet another exemplary embodiment of the present invention, a linear number of the polymorphic genetic markers can be examined. The information associated with the haplotype data may be determined without a need to obtain at least one of first data associated with a pedigree and second data associated with a sub-population of individuals. In addition, further information associated with a confidence level of accuracy of the information can be obtained. A resolution and the further information may be proportional to an amount of effort associated with the determination of the information.

DETAILED DESCRIPTION OF THE INVENTION

Figure 1:
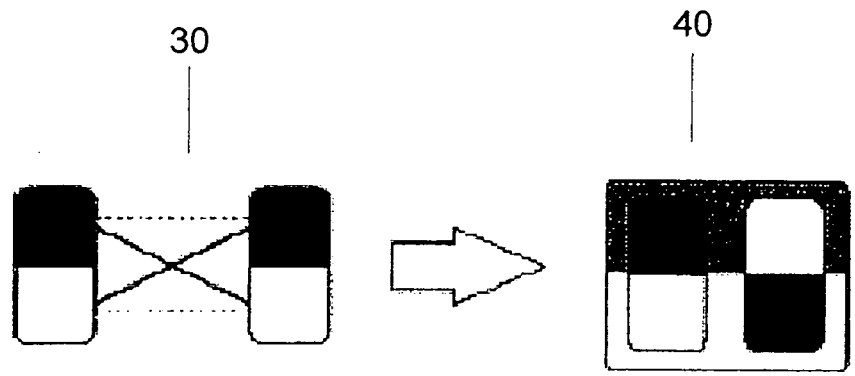
FIG. 1 shows an exemplary collapse of the phase of two polymorphic loci into a single haplotype according to an exemplary embodiment of the present invention.

The problem of reconstructing two haplotypes from genotype data generated by general mapping techniques can be considered according to the exemplary embodiment of the present invention, with a focus on single molecule methods. The genotype data is a set of observations $D = \langle d_i \rangle_{i \in [1 \ldots N]}$. Each observation is derived from one of the two distinct but unknown haplotypes. Each observation $d_i = \langle d_{ij} \rangle_{j \in [1 \ldots M]}$ is a set of observations over the loci index j with $d_{ij} \in R^r$.

Mapping processes are subject to noise, for which a Gaussian model $d_{ij} \sim N(\mu, \sigma)$ with parameter $\mu$ depending on the underlying haplotype of $d_i$ can be assumed. Mapping processes are designed to discriminate the polymorphic allele types in the data space for each locus. Hence, the set of observation points $\langle d_{ij} \rangle_{i \in [1 \ldots N]}$ can be derived from a mixed distribution, which may display bimodal characteristics in the presence of a polymorphic feature. By estimating the parameters of the distribution, a posteriori distribution that a particular point in $R^r$ may be derived from an allele type can be assigned.

Since the mapping errors for $d_{ij}$ and $d_{ij'}$ can be assumed to be independent, determining and computing the posteriori distribution for haplotypes with product allele types is likely straightforward, and is one of the advantages of utilizing single molecule methods in association studies.

One of the problems of phasing is to determine which haplotypes are most likely to account for the observed genotype data. It is preferable to establish the phase by inferring the most likely parameter correlations across the loci index accounting for the posteriori distribution.

Mapping Techniques

The system, method and software arrangement according to an exemplary embodiment of the present invention is applicable to datasets generated by a wide spectrum of mapping techniques. In this manner, a large number of polymorphic markers of different types (e.g. SNPs, RFLPs, micro-insertions and deletions, satellite copy numbers) can be used in an association procedure in accordance with the present invention. An exemplary embodiment of system, method and software arrangement presented herein can utilize mapping techniques capable of a) discriminating alleles at polymorphic loci, and b) providing haplotype data at multiple loci. Other known polymorphic genetic markers may be used by the system, method, and software arrangement according to the present invention.

A mapping technique designed for association studies should preferably be discriminating. In particular, for each polymorphic loci, data points in the data space $R^r$ which are derived from separate allele types should preferably form distinct clusters in the data. One of the exemplary techniques which allows an observation of a single haplotype over multiple loci may preferably be used for an efficient phasing procedure that can be used. For example, single molecule methods may be of exemplary interest. The models and analysis presented herein relates to and is effected by such methods' applicability to association studies.

As an example, the length between two restriction fragments may be considered. The observable $\chi$ may be modeled as a random variable depending on the actual distance $\mu$.

$$P(x \mid \mu) = \frac{1}{\sqrt{2\pi\mu}} \exp\left(\frac{-(x-\mu)^2}{2\mu}\right)$$

Then, it is possible to isolate a specific pair of restriction sites on one of the haplotypes $H_1$, and let the distance between them be provided by $\mu_1$. The distance between the homologous pair on the second haplotype $H_2$ can be provided by $\mu_2$. An observation $\chi$ from the genotype data can then be either derived from $H_1$ or $H_2$, denoted $\chi \sim H_1$ and $\chi \sim H_2$, respectively.

$$P(x) = P(x \mid x \sim H_1)P(x \sim H_1) + P(x \mid x \sim H_2)P(x \sim H_2)$$

$$= \frac{1}{\sqrt{2\pi\mu_1}} \exp\left(\frac{-(x-\mu_1)^2}{2\mu_1}\right) P(x \sim H_1) +$$

$$\frac{1}{\sqrt{2\pi\mu_2}} \exp\left(\frac{-(x-\mu_2)^2}{2\mu_2}\right) P(x \sim H_2).$$

Using the RFLP sizing mapping technique, observable $d_{ij}$, can have independent error sources depending on loci-specific parameters. The set $\{d_{ij}, i\epsilon[1 \ldots N]\}$ can provide points in R which may be discriminated using, e.g., a Gaussian Mixture model. Due to the uncertainty of mapping and underlying haplotypes, posterior distribution $\alpha(x) = [P(x \sim H_1), P(x \sim H_2)]$ can be selected to model the data rather than determined allele types.

The additional description of the exemplary embodiment of the present invention is organized into the following four sections: Section 1 describes the EM-Algorithm procedure used with the exemplary embodiment of the present invention, Section 2 discusses the phasing problem, addressed by the present invention, Section 3 describes a procedure implementation and examples thereof, and Section 4 describes results and applications of the present invention.

Section 1. EM-Algorithm for Detection of Bi-Allelic Polymorphisms of the Present Invention The use of the EM-Algorithm for inferring parameters of a Gaussian mixture model is a well-known technique (see Dempster et al., 1977, J. Roy. Stat. Soc. 39:1-38; and Roweis et al. 1999, Neural Computation 11:305-345), and, as described herein, also useful in the detection of biallelic polymorphisms. In the presence of polymorphisms at loci j, informative mapping data can provide a bimodal distribution in the data space $R^r$. Detailed exemplary computations for E-Step and M-Step of the EM-Algorithm are described herein in the Examples section. For each locus j, the EM-algorithm can be executed in accordance with the present invention until convergence occurs, the result being: $\langle \alpha_k(x), \hat{\Phi} = \langle \hat{\mu}_1, \mu_2, \ldots, \mu_K, \sigma \rangle \rangle$. In this example, $\alpha$ is a posteriori probability that data point x is derived from allele type $k\epsilon[1, 2, \ldots, K]$.

Criteria for Polymorphisms.

Let $\hat{\Phi}$ (D) denote the limit of the EM-algorithm with data set D at the loci j. The following issue may be raised: when will a locus exhibit two specific allele variations? In the setting when K=2, as in the remainder of this description (hence $\hat{\Phi} = \langle \mu_1, \mu_2, \sigma \rangle$), polymorphic loci are defined as events:

$$X(D) = \begin{cases} 1 & \text{if } \hat{\Phi}(D): |\hat{\mu}_1 - \hat{\mu}_2| - \delta > 0 \\ 0 & o.w. \end{cases}$$

Effectiveness of the EM-Algorithm.

Mapping techniques may contain errors that are Gaussian across a diverse set of technologies. Genetic markers may be associated or linked to allele types in the population. The mixture model/technique treated with EM Algorithm can operate effectively, and possibly distinguishing fits beyond visual accuracy. The constraint for a single value of a can force the EM-Algorithm to result in one of two steady states, e.g., $\mu_1 \neq \mu_2$ or $\mu_1 = \mu_2$ (a single Gaussian). Although the EM-Algorithm estimates are slightly biased, the estimators are consistent, and the bias is known to diminish with larger data sets.

The individual experimental data $\{d_{ij}: i\epsilon[1 \ldots N]\}$ can be mapped to posteriori probability that measures over the allele classes. Thus, a probability function $\alpha(y)$ reflecting a confidence (in the presence of mapping error) that point y corresponds to one of our allele types can be produced. For polymorphism assignments, false positives are unlikely to disturb the phasing, while false negatives may affect the size of phased contigs.

Section 2. Phasing Genotype Data

"Phasing" is the problem of determining the association of alleles, due to a linkage on the same haplotype. Letting $\Lambda_j$ be the allele space at loci j, a haplotype may be considered an element of the set: $\Pi_{j\epsilon[1, 2, \ldots, M]} \Lambda_j$.

In phasing polymorphic alleles for an individual's genotype data (a mix of two haplotypes), it can be assumed that about half of the data can be derived from each of the underlying haplotypes $H_1$ and $H_2$. In this context, haplotypes have a complementary structure in that the individual's genotype should be heterozygous at each polymorphic locus.

A haplotype space can be defined in accordance with the present invention, and methods for estimating the probability that an observation $d_i$ is derived from a particular haplotype over a set of loci are described. The maximum likelihood problem for haplotype inference can then be formulated, and this formulation may be the proposed solution to the phasing problem.

Haplotype Space and Joint Distributions.

The full space of haplotypes is the product over all allele spaces $\{1, 2, \ldots, M\}$. In general, haplotype space is in one-to-one correspondence with $M=\{-1, 1\}^M$. The discrete-measure space $(M, 2^M)$ can be used to denote the haplotypes, while $M[j_1, j_2, \ldots, j_v]$ denotes the haplotypes over the range of loci $j_1, j_2, \ldots, j_v$. The result of phasing genotype data may be a probability measure on the space $(M, 2^M)$. Noiseless data may result in a measure assigning ½ to each of the complementary haplotypes, and 0 to all others. This uniform measure over complements corresponds to perfect knowledge of what the haplotypes are. The procedure that can be used by an exemplary embodiment of the system, method and software arrangement of the present invention is consistent in that the correct result is achieved for suitably large data sets.

For example, let $\Lambda_j$ be the allele set for the polymorphic loci j. Two bi-allelic loci j and j' can be used. For clarity, we will assume that $\Lambda_j=\{A, a\}$ while $\Lambda_{j'}=\{B,b\}$. A data observation $d_i$ may be derived from one of the four classes: AB, Ab, aB, ab. Because the mapping noise at loci j and j' are independent, the probability (based on the loci a posteriori) that the observation can be derived from the following four classes:

$$P(d_i \sim AB) = \alpha_{jA}(d_{ij})\alpha_{j'B}(d_{ij'})$$

$$P(d_i \sim Ab) = \alpha_{jA}(d_{ij})\alpha_{j'b}(d_{ij'}) = \alpha_{jA}(d_{ij})(1-\alpha_{j'B}(d_{ij'}))$$

$$P(d_i \sim aB) = \alpha_{ja}(d_{ij})\alpha_{j'B}(d_{ij'}) = (1-\alpha_{jA}(d_{ij}))\alpha_{j'B}(d_{ij'})$$

$$P(d_i \sim ab) = \alpha_{ja}(d_{ij})\alpha_{j'b}(d_{ij'}) = (1-\alpha_{jA}(d_{ij}))(1-\alpha_{j'B}(d_{ij'}))$$

$\alpha_{jj'}^{(i)}$ can be defined as the estimated probability distribution for observation i on haplotypes over the loci j, j':

$$\alpha_{jj'}^{(i)} = [\alpha_{jj'AB}(d_i), \alpha_{jj'Ab}(d_i), \alpha_{jj'ab}(d_i)]$$

$\alpha_{jj'}$ is defined as the estimated probability distribution over the data set on haplotypes over the loci j, j':

$$\alpha_{jj'}(D) = \frac{1}{N}\sum_{i=1}^{N} \alpha_{jj'}^{(i)}$$

For $\rho \in M[j_1, j_2 \ldots, j_M]$ and $\alpha_{j_w \rho_w}(d_i) = \text{Prob}(d_i \sim \rho_w)$ with $\rho_w \in \Lambda_{j_w}$, the estimates can be extended to any set of indices producing:

$$\alpha_{j_1 j_2 \ldots j_M}^{(i)} = \left[\prod_{w \in [1 \ldots v]} \alpha_{j_w \rho_w}(d_i)\right]_{\rho \in M[j_1, j_2, \ldots, j_0]}$$

$$\alpha_{j_1 j_2 \ldots j_M} = \frac{1}{N}\sum_i \alpha_{j_1 j_2 \ldots j_M}^{[i]}$$

Complementarity.

In phasing the diploid genotype data into two haplotypes $\rho_1, \rho_2 \in M$, there may be a special property present, e.g., haplotype $\rho_2$ can be complementary to haplotype $\rho_1$. The complementary pair of haplotypes may be represented $\bar{\rho}_s = \rho_1$. By a change of variables $\omega \in \{-1,1\}^{M-1}$, and the transformation to the haplotypes may be given by the map:

$$\rho_1(b) = \begin{cases} -1 & \text{if } b = 1 \\ -1 \prod_{j=1:(b-1)} w(j) & \text{for } b \in [2 \ldots M] \end{cases}$$

$$\rho_2(b) = \begin{cases} 1 & \text{if } b = 1 \\ 1 \prod_{j=1:(b-1)} w(j) & \text{for } b \in [2 \ldots M] \end{cases}$$

In evaluating the data, there may be a possible $2^{M-1}$ complementary pairs of allele types to search.

The confidence of a set of complementary haplotypes can be modeled as a probability distribution on the discrete measure space $\langle M, 2^m \rangle$, which is the convex hull of the following set of extremal points which correspond to certain knowledge of complementary haplotypes.

$$A = \left\{\theta_\rho : \theta_\rho(\delta) = \begin{cases} \frac{1}{2} & \text{if } \delta = \rho \\ \frac{1}{2} & \text{if } \delta = \bar{\rho} \quad \text{for } \delta \in M \\ 0 & o.w. \end{cases}\right\}$$

These values can represent the uniform distribution over complementary haplotypes and geometrically are vertices of a high dimensional hypercube. For example, let $A[j_1, j_2, \ldots, j_v]$ be the corresponding distribution over the haplotype space $M[j_1, j_2, \ldots, j_v]$.

Maximum Likelihood Problem.

For every loci j, it can be assumed that the data $\{d_{ij} : i \in [1 \ldots N]\}$ contains an equal distribution of data from the underlying haplotypes $H_1, H_2$ that can be inferred. Using the estimated values $\alpha$ for the joint distribution over loci product spaces, the haplotypes most likely producing $\alpha$ can be computed. The corresponding maximum likelihood problem may be formulated as follows:

Let the likelihood function be given by:

$$L(\theta) = P(D \mid \theta) = \frac{\Gamma(N)}{\prod_{\rho \in M} \Gamma(N\alpha_\rho)} \prod_{\rho \in M} \theta_\rho^{\alpha_\rho N}$$

MLE1 Find $\rho \in A$ so that $L(\rho) \geq L(\omega) \forall \omega \in A$.

Similarly, for any specified set of loci $\{j_1, j_2, \ldots, j_v\}$, a likelihood function $L_{M[j_1, j_2, \ldots, j_v]}$ may be defined as the most likely to produce posterior $\alpha_{j_1, j_2, \ldots, j_v}$ over the space $M[j_1, j_2, \ldots, j_v]$.

Lemma 1 If $d(\alpha, A) < \epsilon$ for some $\epsilon$ small enough, and $d(\alpha, A) = \min_{\theta \in A} \|\alpha - \theta\|_2$.

Maximizing $\prod_{\rho \in \{0,1\}^{M-1}} \theta_\rho^{\alpha_\rho N}$ over $\theta \in A$ is equivalent to minimizing $$\sum_{j \in [1 \ldots M]} \frac{(\alpha_j - \theta_j)^2}{\alpha_j} \text{ over } \theta \in A.$$

The description provided below in the Examples section is derived from a Taylor-series expansion of the likelihood function. It demonstrates that the MLE result in set A is the vertex of a $2^{M-1}$ hyper-cube closest to the estimated joint probability function $\alpha$, measured by a modified $L_2$ norm.

With this result, the following function to be used in the algorithms presented later can be assumed:

---
Algorithm 1
---
MLE-COLLAPSE($j_1, j_2, \ldots, j_v$)
    Compute $\rho \in A[j_1, j_2, \ldots, j_v]$
        minimizing $\Sigma_{j \in [j_1, j_2, \ldots, j_v]} \frac{(a_j - \theta_j)^2}{a_j}$ over $\theta \in A$
    return $\rho$
---

Section 3. Exemplary Procedures

Exemplary procedures generally focus on growing disjoint-phased contiguous sets of loci called contigs. For example, all loci can be assigned an arbitrary phase and begin as a singleton phased contig. A JOIN operation checks if these phased contigs may be phased relative to one another using a function called VERIFY-PHASE. VERIFY-PHASE can be designed to check a phasing criteria, for example refuting a hypothesis of Hardy-Weinberg Equilibria is discussed below in the Examples section. Other examples of suitable phasing criteria are known to those of ordinary skill in the art. Such criteria may, for instance, be based on the statistical distribution of haplotypes in the ambient population, on the perfect phylogeny hypothesis, or on the relation to genotypes of parents, siblings and other closely-related family members.

If a pair of phased contigs can be joined by passing the test, implied by VERIFY-PHASE function, then the disjoint sets are combined into a single phased contig and the joint distribution over the set is computed with the MLE-COLLAPSE function. After completion of a successful join operation, the resulting distribution function may be regarded as the most likely one among all haplotypes that can generate the observed data over the specified loci. Because the growth of contigs is monotonic and depends on local information available at the time of the operation, an ADJUST operation is also considered that fractures and rejoins contigs using a larger locality of data than what was available during the JOIN.

The operations are described in detail, the results are analyzed, and methods for avoidance of incorrect operations are indicated.

Collapse.

Figure 2:
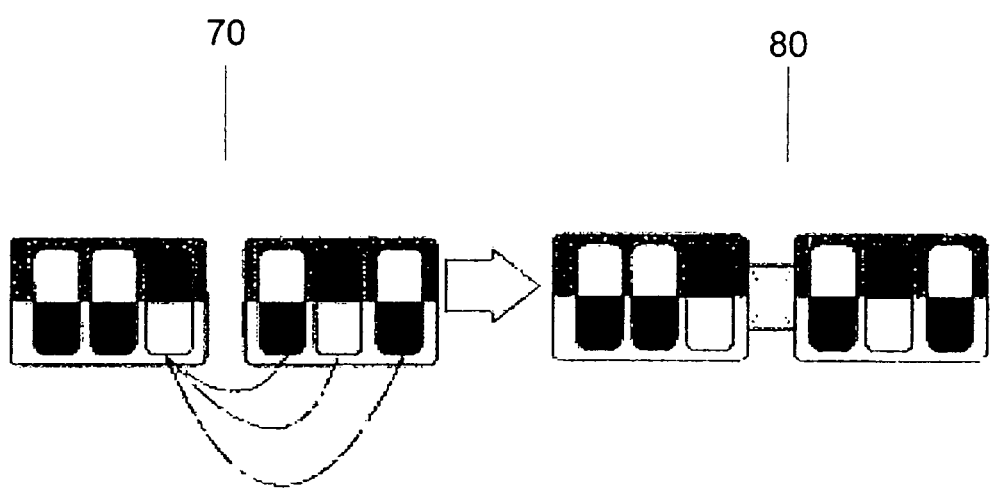
FIG. 2 shows an exemplary illustration of the phase of three polymorphic loci provided into two complementary haplotypes in accordance with the exemplary embodiment of the present invention.

The collapse of the phase operation can be described as the MLE-COLLAPSE function, the example of which is shown in FIG. 1 which provides a collapse of the phase of two polymorphic loci 30 into a single haplotype 40. It may be used to update a joint probability distribution over a set of contigs, and has the effect of keeping the contig structures bound to haplotype states which simplifies the computing of a phase. FIG. 2 shows an exemplary illustration of the phase of three polymorphic loci 70 provided into two complementary haplotypes 80 in accordance with an exemplary embodiment of the present invention Join:

Let K be a parameter denoting neighborhood size. Let $C_1 = \{j_1, j_2, \ldots, j_v\}$ and $C_2 + \{j_1', j_2', \ldots, j_w'\}$; then the join operation is as follows:

Given joint-probability functions $\alpha_{j_1}, \alpha_{j_2}, \ldots, \alpha_{j_v}, \alpha_{j'_1}, \alpha_{j'_2}, \ldots \alpha_{j'_w}$, compute the joint probability function $\alpha_{C_1, C_2}$ with formula $$\alpha_{c_1, c_2} = \alpha_{(j\omega)(j_1, j_2, \ldots, j_\omega)} \approx \omega_{j_e j_1} \alpha_{(j_e)(j_1, j_2, \ldots, j_w)} +$$
$$\omega_{j_1, j_2} \alpha_{(j_e)(j_1, j_e \ldots j_w)} + \ldots + \omega_{j_w, j_k} \alpha_{(j_w)(j_1, j_2, \ldots, j_w, \ldots, j_\omega)}$$

with $$\alpha_{(j_1)(j_1, j_2, \ldots, j_z, \ldots, j_w)} = \sum_{i=1:N} \alpha^{(i)}_{j_w j_z} = \sum_{i=1:N} \alpha^{(i)}_{j_\omega}(d_{i, j_\omega}) \alpha^{(i)}_{j_z}(d_{i j_z})$$

$$\omega_{j_w j_z} = k \frac{1}{d(j_v, j_z)}$$

Here, $$\frac{1}{\frac{1}{d(j_v, j_1)} + \frac{1}{d(j_v, j_2)} + \ldots + \frac{1}{d(j_v, j_k)}} \text{ and } d(j_v, j_z)$$

and $d(j_v, j'_x)$ is proportional to genomic distance between loci $j_v$ and $j'_x$.

---
Algorithm 2
---
COMPUTE-PHASE( $C_1 = \{j_1, j_2, \ldots, j_v\}$, $C_2 = \{j'_1, j'_2, \ldots, j'_w\}$, K )
    assume $j_v$ in $C_1$ is such that $d(j_v, C_2) \leq d(j, C_2)$ $\forall j \in C_1$:
    Compute $\alpha_{(j_v)(j'_1 j'_2 \ldots j'_v)}$ using parameter K
    return $\alpha_{(j_v)(j'_1 j'_2 \ldots j'_v)}$
---

---
Algorithm 3
---
JOIN( $C_1 = \{j_1, j_2, \ldots, j_v\}$, $C_2 = \{j'_1, j'_2, \ldots, j'_w\}$, K )
    COMPUTE-PHASE( $C_1 = \{j_1, j_2, \ldots, j_v\}$, $C_2 = \{j'_1, j'_2, \ldots, j'_w\}$, K )
    if ( VERIFY-PHASE( $\alpha_{j_1 j_2 \ldots j_v}$ ) ) then
        $\alpha_{j_1 j_2 \ldots j_v} \leftarrow$ MLE-COLLAPSE($j_1, j_2, \ldots, j_v$),
---

The method, system and software arrangement of an exemplary embodiment according to the present invention can estimate the haplotypes by solving an ordered set of local MLE problems.

Implementation.

Input. The input is a set of data points $\{d_{ij} \in R^r: i \in [1 \ldots N], j \in [1 \ldots M]\}$. The following assumptions are made about the input:

For each j the points $d_{1j}, d_{2j}, \ldots, d_{Nj}$ are derived from the Gaussian mixture model corresponding to mapping data at polymorphic loci j.

For each i points $d_{i1}, d_{i2}, \ldots, d_{iM}$ are independent random variables with parameters associated to underlying haplotypes.

With the knowledge of the mapping order of polymorphic loci, the positions of the genome can be assumed to be $\chi_1, \chi_2, \ldots, \chi_M$.

Implementation.

Pre-Process. The EM-algorithm procedure can be executed for each locus: $\{d_{ij}: i \in [1 \ldots N] \text{ observable }\} \rightarrow \{\hat{\Phi}_j : \alpha_j\}$ $\forall j \in [1, \ldots, M]$.

The result is a set of estimates for bi-allelic loci, $\{\hat{\Phi}_1, \hat{\Phi}_2, \ldots, \hat{\Phi}_M\}$, as well as a set of functions estimating the probability that any data point derives from the distinct alleles $\{\alpha_1, \alpha_2, \alpha_M\}$.

Next, a join schedule can be constructed. Letting $\beta_j = \chi_{j+1} - \chi_j$, the results are sorted into an index array giving an increasing sequence: $j_1, j_2, \ldots j_v, \ldots j_{m-1}$.

Implementation.

Main Algorithm and Data Structure. Contigs can be maintained in a modified union-find data structure designed to encode a collection of disjoint, unordered sets of loci, which may be merged at any time. Union-find supports two operations, UNION and FIND (see Tarjan, 1983, Data Structures and Network Algorithms, CBMS 44, SIAM, Philadelphia). For example, UNION can merge two sets into one larger set, and FIND can identify the set containing a particular element. Loci j may be represented by the estimated distribution $\alpha_j$, and can reference its left and right neighbor. At any instant, a phased contig may be represented by:

An MLE distribution or haplotype assignment for the range of loci in the contig (if one can be evaluated).

Boundary loci: Each contig has a reference to left- and right-most locus.

In the vth step of the procedure, consider the set of loci determined by $\beta_{j_v}$, $\{j_v, j_{v+1}\}$: If FIND $(j_v)$ and FIND $(j_{v+1})$ are in distinct contigs $C_p$ and $C_q$, then (a) attempt to UNION $C_p$ and $C_q$, by use of the JOIN operation, and (b) update the MLE distribution and boundary loci at the top level if the JOIN is successful.

Implementation.

Output. Output can be a disjointed collection of sets, each of which is a phased contig. It represents the most likely haplotypes over that particular region.

Implementation.

Time Complexity. The preprocess may involve using the EM-algorithm/procedure once for each locus. The convergence rate of the EM-algorithm procedure has been analyzed (see Ma et al., 2000, Neural Computation 12:2881-2907) and depends on the amount of overlap in the mixture of distributions. For moderate-sized data sets, no difficulties with convergence of the EM-algorithm procedure have been observed.

The time complexity of the main exemplary procedure can be estimated by implementing the K-neighbor version. For each $\beta_{j_v}$ there may be two find operations. The number of union operations preferably does not exceed the cardinality of the set $\{\beta_j, j \in [j_1, j_2, \ldots j_{M-1}]\}$, as contigs grow monotonically. The time-cost of a single "find" operation is preferably at most $\gamma(M)$, where $\gamma$ is the inverse of Ackermann's function. Therefore, the time cost of all union-find operations is preferably at most $O(M\gamma(M))$. The join operation, on the other hand, uses the execution of the K-neighbor optimization routine, at a cost of $O(K)$. Thus, the main exemplary procedure has a worst-case time complexity of $$O(M(\gamma(M)+K))=O(M\gamma(M))$$

and may be regarded as approximately linear in the number of markers, M for all practical purposes, since K is likely a small constant.

Examples

RFLP Examples

Figure 3:
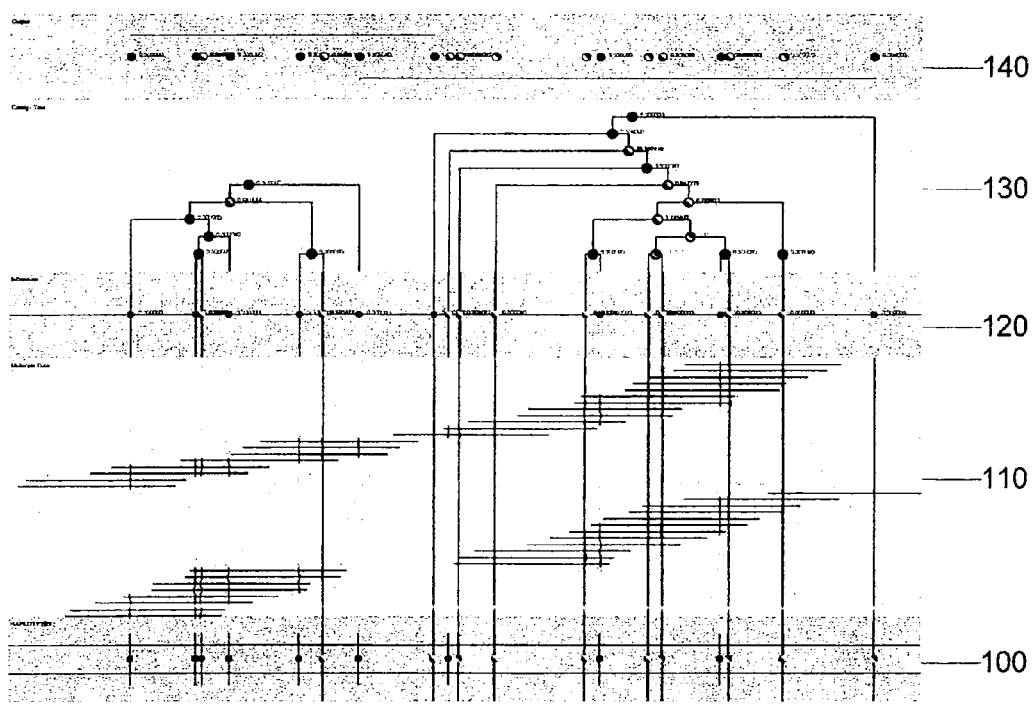
FIG. 3 shows an illustration of exemplary haplotypes determined by application of the system, method and software arrangement according to the exemplary embodiment of the present invention to Dataset I.

The method, system and software arrangement of the exemplary embodiment of the present invention can be demonstrated on two simulated data sets composed of ordered restriction fragment lengths subject to sizing error. FIG. 3, which shows exemplary haplotypes, obtained using such exemplary embodiment is presented in the following bands:

The band 100 nearest the bottom in the layout is the simulated haplotype.

The second band 110 from the bottom is the haplotype molecule map for a diploid organism. These molecules (which are sorted into two haplotype classes in the layout) can be mixed and made available to the procedure of the present invention as a single set of genotype data.

The third band 120 from the bottom shows the results of the EM-algorithm and the set of markers that are determined to have polymorphic alleles.

The fourth band 130 in the layout provides the history of contig operations. From this tree, it is possible to view: 1) the developing k-neighborhoods, and 2) the distinct phased contigs.

The top band 140 in the layout provide the algorithmic output for this problem, including phased-in subsets that span the distance indicated by the bars above and below the loci markers. The areas where phase structure overlaps but cannot extend are regions that are of interest to target with more specific sequences, in order to extend the phasing.

Parameters of the simulations are summarized in Table 1.

TABLE 1

Parameters* employed in performing the simulations for Datasets 1 and 2.

| Parameter | Symbol | Data Set 1 | Data Set 2 |
|---|---|---|---|
| Number of molecules | M | 80 | 150 |
| Number of fragments RFLP and non RFLP | F | 20 | 100 |
| Size of the genome | G | 12000 | 50000 |
| Expected molecule size | EMS | 2000 | 2000 |
| Variance in molecule size | VMS | 50 | 500 |
| Variance in fragment length size | VFS | 1 | 20 |
| P-value that any given fragment is an RFLP | P-BIMODE | .5 | .3 |
| Expected separation of means for RFLP | ERFLPSEP | 10 | 50 |
| Variance in the separation of means for RFLP | VRFLPSEP | .01 | 6 |

*Any parameter with both an expectation and variance can be generated with a normal distribution.

A simple VERIFY-PHASE function which checked that the posteriori distribution $C_a, C_b$ is separated by a distance of $C > 0$ from the point $$\left[\frac{1}{2}, \frac{1}{2}\right]$$

may be used as an example. In practice, it was discovered that the parameter C should preferably depend on the local coverage.

For the first simulation on dataset I, shown in FIG. 3, a relatively small set was chosen so that the potential limitations of the procedure may be revealed. Here the neighborhood size was set to k=5. False positive RFLP detections were not guarded against, yet phasings are computed. It is clear that mistakes provided therein were likely due to the low coverage library.

Figure 4:
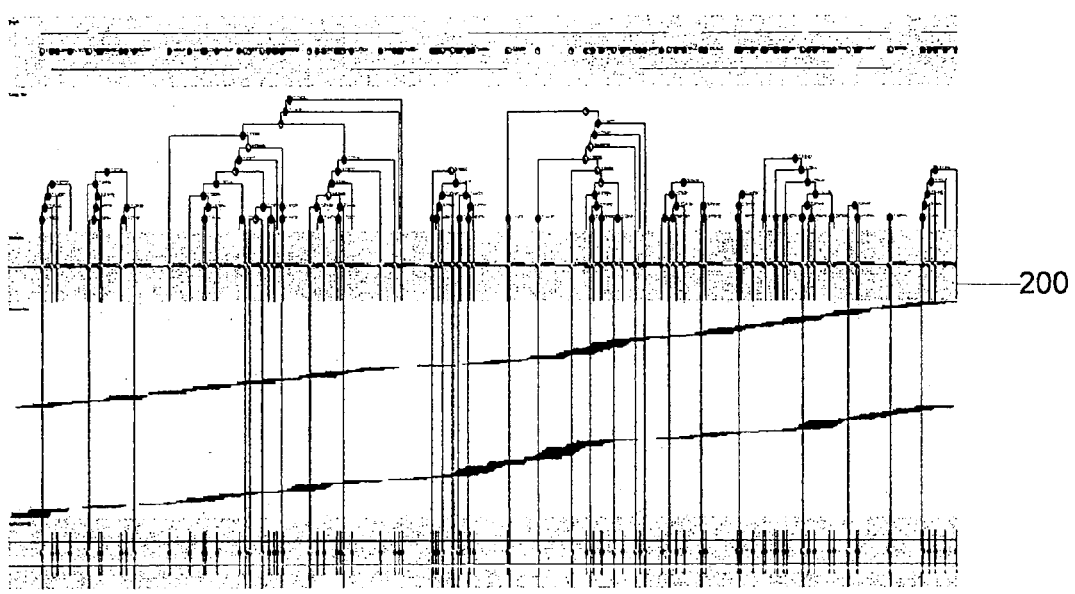
FIG. 4 shows an illustration of exemplary haplotypes determined by application of the system, method and software arrangement according to the exemplary embodiment of the present invention to Dataset II.

In the second simulation on dataset II, seen in FIG. 4, the result 200 shows that good phasing results may be achieved even on large, sparse data sets.

MLE Estimate

If $d(\alpha, A) < \epsilon$ for some $\epsilon$ small enough. Maximizing $\Pi_{p \in (0,1)} {}^{M-1} \theta_p^{\alpha pN}$ over $\theta \in A$ is equivalent to minimizing $$\sum_{j \in [1 \ldots M]} \frac{(\alpha_j - \theta_j)^2}{\alpha_j}$$

over $\theta \in A$.

Proof. Let $$F(\theta) = \frac{n!}{\prod_{j \in [1 \ldots M]} n_j} \prod_{jm1:k} \theta_j^{n_j}.$$

Computing the second variation:

$$F''(\theta) = \left( \begin{bmatrix} \frac{n_1^2}{\theta_1^2} & \frac{n_1 n_2}{\theta_1 \theta_2} & \cdots & \frac{n_1 n_k}{\theta_1 \theta_k} \\ \frac{n_2 n_1}{\theta_2 \theta_1} & \frac{n_1^2}{\theta_1^2} & \cdots & \frac{n_2 n_k}{\theta_2 \theta_k} \\ \vdots & \vdots & \ddots & \vdots \\ \frac{n_2 n_1}{\theta_2 \theta_1} & \frac{n_2 n_2}{\theta_2 \theta_1} & \cdots & \frac{n_k^2}{\theta_k^2} \end{bmatrix} - \begin{bmatrix} \frac{n_1}{\theta_1^2} & 0 & \cdots & 0 \\ 0 & \frac{n_2}{\theta_1^2} & \cdots & 0 \\ \vdots & \vdots & \ddots & \vdots \\ 0 & 0 & \cdots & \frac{n_k}{\theta_k^2} \end{bmatrix} \right) F(\theta)$$

Since $F(\theta)$ is smooth in $\theta$, Taylor's remainder theorem gives, $$F(\theta) = F(\alpha) + \nabla F(\alpha) \cdot (\theta - \alpha) + (\theta - \alpha)^T F''(\alpha)(\theta - \alpha) + o(\|(\theta - \alpha)\|_2)$$

When $$\alpha = \left| \frac{n_1}{n} \ldots \frac{n_2 n_1}{n} \right|,$$

$\nabla f(\alpha) = 0$, this is a standard MLE result for a multi-nominal distribution. Computing the quadratic function:

$$(\theta - \alpha)^T F''(\alpha)(\theta - \alpha) = (\theta - \alpha)^T \left( n^2 \begin{bmatrix} 1 & 1 & \cdots & 1 \\ 1 & 1 & \cdots & 1 \\ \vdots & \vdots & \ddots & \vdots \\ 1 & 1 & \cdots & 1 \end{bmatrix} - n \begin{bmatrix} \frac{1}{\alpha_j} & 0 & \cdots & 0 \\ 0 & \frac{1}{\alpha_j} & \cdots & 0 \\ \vdots & \vdots & \ddots & \vdots \\ 0 & 0 & \cdots & \frac{1}{\alpha_j} \end{bmatrix} \right) F(\alpha)(\theta - \alpha)$$

$$= F(\alpha) n^2 \left( \sum_j (\theta_j - \alpha_j) \right)^2 - F(\alpha) n \sum_j \frac{(\theta_j - a_\alpha)^2}{\alpha_j}$$

$$= -F(\alpha) n \sum_j \frac{(\theta_j - \alpha_j)^2}{\alpha_j}$$

Thus for an $\theta$ bery near to $\alpha$ the level curves of F are given by $\theta_d = \{0 : F(\theta) = F(\alpha) - \delta\}$ are approximately ellipsoids $$F(\theta) = F(\alpha) - F(\alpha) n \sum_j \frac{(\theta_j - \alpha_j)^2}{\alpha_j} + o(\|(\theta - \alpha)\|_2)$$

$$= F(\alpha) - F(\alpha) n \sum_j \frac{(\theta_j - \alpha_j)^2}{\alpha_j} + o\left( \sum_j \frac{(\theta_j - \alpha_j)^2}{\alpha_j} \right)$$

Let $$\|\theta - \alpha\|_\alpha^2 = \sum_j \frac{(\theta_j - \alpha_j)^2}{\alpha_j}.$$

Letting $L_1 = L(\alpha)$ and assuming there is a second local optima for the likelihood function value at $L_2$, let $$V(\alpha) = \left\{ \theta : L(\theta) > L_1 - \frac{L_1 - L_2}{2} \right\}.$$

We must show that there is a $\delta$ so that $\{\theta : \|\theta - \alpha\|_\alpha^2 < \delta\} \subset V(\alpha)$. And this is clear from the inequality $$L_1 - L_1 n \|\theta - \alpha\|_\alpha^2 - o(\|\theta - \alpha\|_\alpha^2) < F(\theta) < L_1 - L_1 n \|\theta - \alpha\|_\alpha^2 + o(\|\theta - \alpha\|_\alpha^2)$$

by choosing $\delta$ small enough that $$L_1 n \delta + o(\delta) < \frac{L_1 - L_2}{2}.$$

We conclude that if there is a point of $A \in \{\theta : \|\theta - \alpha\|_\alpha^2 < \delta\}$ then it must be the unique maxima in A for our likelihood function.

Test for Hardy-Weinberg Equilibria at Different Loci

The Chi-squared statistical test for determining whether allelic data at loci j and j' display linkage disequilibrium, and hence are not in Hardy-Weinberg Equilibrium (HWE) has been reviewed in great detail. See Weir, 1996, Genetic Data Analysis II, Sinauer Associates, Sunderland, Mass. for details and a complete statistical treatment. The Chi-squared statistical test for gametic disequilibrium at two loci has been modified by using additive disequilibrium coefficients to adjust to our population model. The end result is a Chi-squared statistical test that allows the rejection of HWE from observed frequencies alone. Since determination of linkage is a prerequisite to phasing, or at least in finding structure in the joint distribution over allele spaces of adjacent loci, this statistical test is important. The boundaries of haplotype blocks (or phased contigs) are an interesting and important issue in understanding population dynamics.

For example, let $D_{ab}$ denote the disequilibrium coefficient between alleles a at loci j and b at loci j':

$$D_{ab} = p_{ab} - p_a p_b$$

Where $p_{ab}, p_a, p_b$ are the population frequencies for allele type: ab, a, b respectively. In the presence of HWE $D_{ab}$ can be expected to be zero. Letting $\hat{D}_{ab}$ denote an estimate from estimate frequencies:

$$\hat{D}_{ab} = \tilde{p}_{ab} - \tilde{p}_a \tilde{p}_b$$

with:

$$\bar{p}_b = \frac{1}{N} \sum_{i=1:N} \alpha_{bj}(d_{ij}) \cdot \bar{p}_b = \frac{1}{N} \sum_{i=1:N} \alpha_{bj}(d_{ij'})$$

Computation of Expectation and Variance:

$$E(\hat{D}_{ab}) = \frac{N-1}{N} D_{ab}$$

$$V(\hat{D}_{ab}) \approx \frac{1}{N}[p_a q_a p_b q_b + (1-2p_a)(1-2q_a)D_{ab} - D_{ab}^2]$$

The variance can be computed using Fisher's approximate variance formula. Under the assumption that loci j and j' are in HWE, $D_{ab}=0$ and:

$$E_{HWE}(D_{ab}) = 0$$

$$V_{HWE}(D_{ab}) = \frac{1}{N}[p_a q_a p_b q_b]$$

From this information, it is possible to construct a Chi-Squared test to evaluate the hypothesis that alleles a and b at loci j and j' are acting as they would if they were in HWE.

$$X_{ab}^2 = t^2 = \frac{N\hat{D}_{ab}^2}{\bar{p}_a^A \bar{q}_a^A \bar{p}_b^B \bar{q}_b^B}$$

It is possible to reject the HWE hypothesis correctly 9 times in 10 by using a reference value of $z^2 > 2.71$, or we may reject HWE correctly 99 times in 100 using reference values $z^2 > 6.63$. If alleles are linked by a haplotype, this test may be used as the VERIFY-PHASE function mentioned previously in this text.

EM-Algorithm Analytic Results

A. An Example Using RFLP Markers

The data at loci j can refer to the observed distances between restriction sites j and j+1, as they are derived from two haplotypes $H_1$ and $H_2$ with underlying genome distances $\mu_1$ and $\mu_2$. The distribution of data points for loci j is given by:

$$f_j(x) = \frac{1}{\sqrt{2\pi\mu_{j1}^2}} \exp\left(\frac{-(x-\mu_{j1})^2}{2\mu_{j1}^2}\right) \alpha_{j1}(x) + \frac{1}{\sqrt{2\pi\mu_{j2}^2}} \exp\left(\frac{-(x-\mu_{j2})^2}{2\mu_{j2}^2}\right) \alpha_{j2}(x)$$

It is preferable to make a simplifying assumption that $\sigma = 1$; $2(\mu j_1 + \mu j_2)$, so that $f_j$ may be closely approximated by:

$$F_j(x) = \frac{1}{\sqrt{2\pi\sigma^2}} \exp\left(\frac{-(x-\mu_{j1})^2}{2\sigma^2}\right) \alpha_{j1}(x) + \frac{1}{\sqrt{2\pi\sigma^2}} \exp\left(\frac{-(x-\mu_{j2})^2}{2\sigma^2}\right) \alpha_{j2}(x)$$

For loci j the set of points $\{d_{ij} = i \in [1, 2, \ldots N]\}$ is data. It is preferable to infer the model parameters $\Phi = \{\sigma = \mu_1, \mu_2\}$ and posteriori distribution or by use of the EM-algorithm. The subscript j can be dropped in the following equation, the objective being to iteratively optimize the function:

$$H(\alpha, \Phi) = \sum_{i \in 1:\alpha} \sum_{k \in 1:2} (\alpha_k(d_{ji}) \ln G_k(d_{ji} | \Phi) - \alpha_k(d_{ji}) \ln(\alpha_k(d_{ji})))$$

With $$G_k(x | \Phi) = \frac{1}{\sqrt{2\pi\sigma^2}} \exp\left(\frac{-(2-p_r)^1}{2\sigma^2}\right)$$

the kth Gaussian kernel.

Optimization can be done in two steps:

1. B-STEP holding $\phi$ fixed, optimize $H(\alpha, \phi)$ over $\alpha$, letting $\phi$ be the previous estimate of parameters.

The result for the argmax $\alpha$ is:

$$\alpha_k(x) \leftarrow \frac{G_k(x | \phi)}{\sum_1 G_1(x | \phi)}$$

2. M-STEP

Holding $\alpha$ fixed, optimize $H(\alpha, \phi)$ over $\phi$ (using the prevous estimate of parameters on the hidden categories $\hat{\alpha}(\gamma)$, which depend on the previous estimate Donoted $\phi = [\beta_1, \beta_2, \theta]$). The result argmin $H(\hat{\alpha}, \phi)$ is:

$$\mu_k \leftarrow \frac{\sum_{1:n} \delta_k(d_{ij}) d_{ij}}{\sum_{1:n} \delta_k(d_{ij})}$$

$$\sigma \leftarrow \sqrt{\frac{1}{2} \sum_{j\_2} \frac{1}{N} \sum_{1N} d_j(d_{ij})(d_{ij} - \beta_j)^2}$$

The EM-algorithm procedure can be executed until convergence in the parameter space occurs. Exemplary detailed computations for the E-Step and M-Step are provided in the appendix. Detailed proofs of each step are provided below.

E-Step

Proof. Consider the calculus problem of optimizing:

$$f(\phi) = \phi(A_1 - \log(B\phi)) + (1-\phi)(A_2 - \log(B(1-\phi)))$$

$$f'(\phi) = 0 \Rightarrow \phi = \left(\frac{1}{e^{A_1 + A_2} + 1}\right)$$

$\phi \in (0,1)$. Apply this fact to the optimization problem of finding numbers $Q = (\alpha_{iv}) i=1:n, v=1:2$, so that the following function is optimized:

$$\sum_{i=1:n} \sum_{v=1:2} \left( \alpha_{iv} \left( A_{i2} - \log(B_\alpha w) \right) = \sum_{1w1:n} (A_\cap - \log(B\alpha_w)) + (1-\alpha_w)(A_\alpha - \log(B(1-\alpha_w))) \right)$$

Where $$A_1 = \frac{(dj - \mu 1)^2}{2\sigma 2} \text{ and } A_2 = \frac{(dj - \mu 2)^2}{2\sigma 2}$$

and $B=\sqrt{2\pi\sigma^2}$. It is shown that the answer is given by maximizing each summand and hence given by:

$$\overline{\phantom{x}} = \left(\frac{1}{e^{\left(\frac{(d_1 - p_1)^2}{2\alpha^2} \frac{(d_1 - p_2)^2}{2\alpha^2}\right)} + 1}\right) = \frac{G_1(d_i)}{G_1(d_i) + G_2(d_i)}$$

and similarly for $\sigma_2$.

M-Step

Proof. Consider the calculus problem of optimizing:

$$f(\mu_1, \mu_2, \sigma) = \sum_{\_1:N}\sum_{\_1:2} q_{vi}\log\left(\frac{1}{\sqrt{2\pi\sigma^2}}\exp\frac{-(\alpha_i - \mu_v)^2}{2\sigma^2}\right) + H$$

$$= \sum_{im1:N}\sum_{\mu m1:2} q_{vi}\left(\frac{-(\alpha_i - \mu_v)^2}{2\sigma^2} - \log\sqrt{2\pi\sigma^2}\right) + H$$

Where H is constant in ($\mu_1$, $\mu_2$, $\sigma$). Consider the partial derivative of f with respect to $\mu_2$:

$$\frac{\partial f}{\partial \mu_v} = \sum_{i=1_2N} \frac{\partial}{\partial \mu_v}\left(\frac{qw}{2\sigma^2}\left(-\alpha_1^2 + 2\alpha_{1\mu v} - \mu_v^2 - 2\sigma^2\log\sqrt{2\pi\sigma^2}\right)\right)$$

$$= \frac{1}{\sigma^2}\sum_{im1:N} q_{up}\sigma_p - \mu_v q_{vi}$$

Thus, the following is obtained:

$$\frac{\partial f}{\partial \mu_v} = 0 \Leftarrow \mu_v = \frac{\sum_{i=1:N} q_{iv}\alpha_i}{\sum_{i=1:N} q_{iv}}$$

Now consider the partial of $f$ with respect to $\sigma$:

$$\frac{\partial f}{\partial \sigma} = \sum_{i=1:N}\sum_{v=1:2} q_{vi}\left(\frac{(\alpha_i - \mu_i)^2}{2\sigma^2} - 1\right)$$

Section 4. Conclusions

The simulation results described herein demonstrate that locally the phasing may be highly accurate. When local coverage derived from one haplotype is low, the detection of polymorphisms can become difficult. In the first dataset, a false negative detection may be found on the $8^{th}$ marker from the left. This false negative was due to zero coverage from one of the haplotypes at that point. The ninth marker can be a false positive detection, and may be attributed to zero coverage from one haplotype and low coverage (two molecules) from the alternative haplotype. The false positive does not cause errors in the phase information for correctly detected polymorphic loci in the phased-contig achieved over marker index in the set {7, 8, 9, 10, 11, 12, 13, 14, 15, 16, 17, 18, 19}. Designing a mapping experiment targeting a polymorphic marker in the set {6, 7, 8, 9, 10} can allow one to phase the two contigs into a single contig.

The results of the method for haplotype phasing of the present invention may be assessed in terms of two absolute quantities: resolution and accuracy. Not only does the method of the present invention provide conclusions, it also reports a confidence level associated with the conclusion. Since an individual's haplotype structure is singular and absolute, any method that makes conclusions about that structure should assess its own accuracy. The method according to the present invention provides this assessment in such a way that the resolution and accuracy of the conclusions drawn for an individual scale with the amount of effort (i.e. mapping experiments) expended on that individual. This feature of the method is important because (a) an accurate and high resolution determination of an individual's haplotype structure may be drawn in the absence of knowledge or information from her/his pedigree or sub-population, in contrast to population-based studies, which rely on mapping data from a set of closely related individuals, and (b) since resolution and accuracy scale with effort, the same scaling relationship is present for cost. In various applications of the method and system of the instant invention where different resolutions and accuracies are required, the present method provides a better estimate for the same cost when compared to currently available alternative methods.

Figure 5:
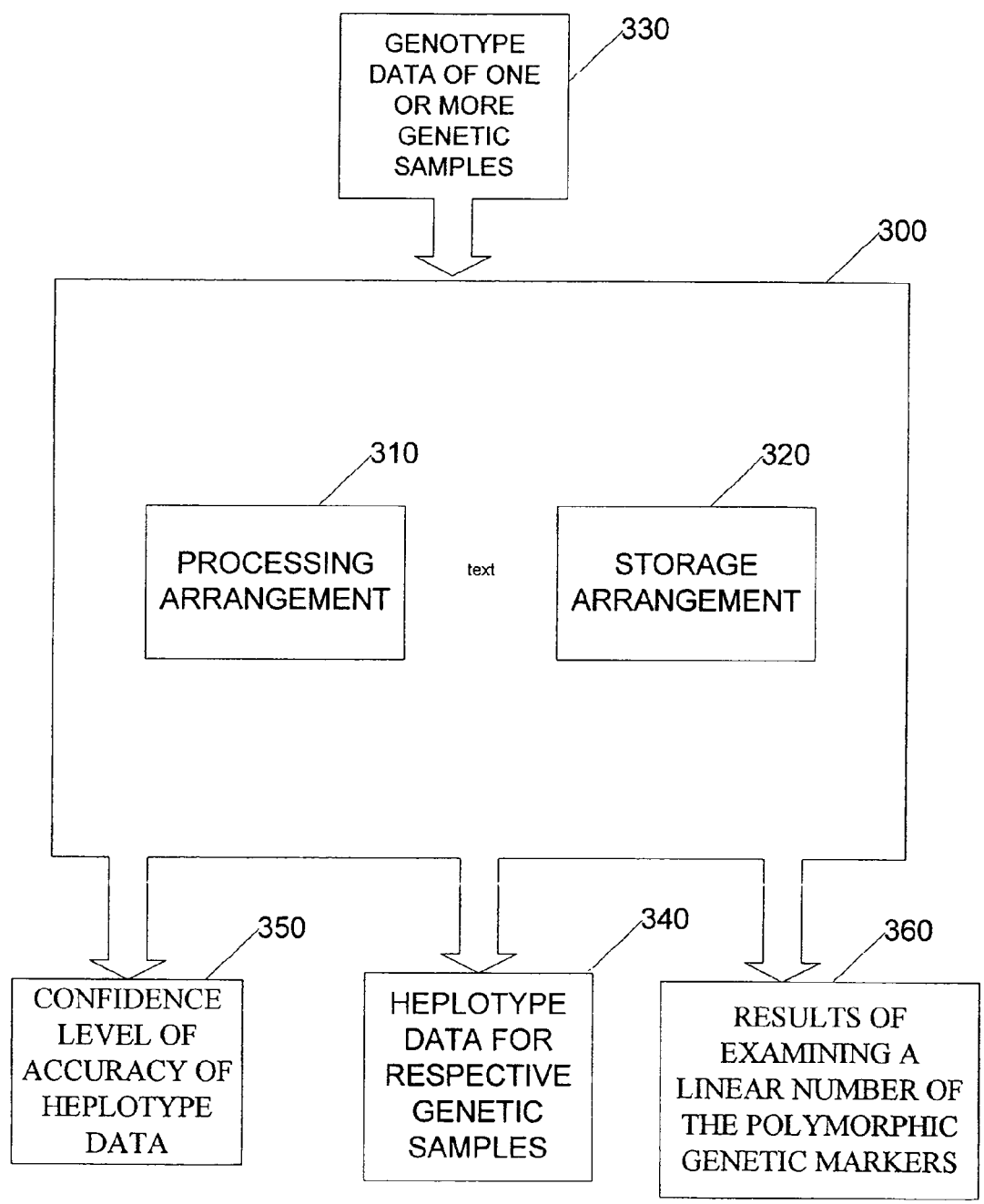
FIG. 5 shows a block diagram of an exemplary embodiment of a system according to the present invention which is capable of storing thereon the storage arrangement of the present invention, and operable to execute thereon the method according to the present invention.

FIG. 5 shows a block diagram of an exemplary embodiment of a system 300 according to the present invention which is capable of storing thereon the storage arrangement of the present invention, and operable to execute thereon the method according to the present invention.

In particular, the system includes a processing arrangement 310 and a storage arrangement 320. The storage arrangement 320 can be one or more hard drives, memory (read-only memory, random access memory—"RAM". DRAM). CD-ROMs. floppy disks. etc. and/or combination thereof, and may store thereon a software arrangement (e.g., a software program). The software program can be accessed by the processing arrangement 310 (e.g., a processor such as Intel Pentium® processor), and the software arrangement can make the processing arrangement operable to execute the exemplary embodiment of the present described herein.

For example, the system 300 can receive genotype data associated with one or more genetic sample, either from external sources or from the storage arrangement 320. The processing arrangement 310 (executing the software arrangement obtained from the storage arrangement 320) obtains the data, and performs the procedures in accordance with the exemplary embodiment of the present invention. After the processing is completed by the processing arrangement 310, the processing arrangement can obtain and output haplotype data for respective genetic sample (in block 340). In addition or as an alternative, the processing arrangement 310 can obtain a confidence level of accuracy of the obtained haplotype data (block 350), and/or results of examination of a linear number of polymorphic genetic markers (block 360).

Figure 6:
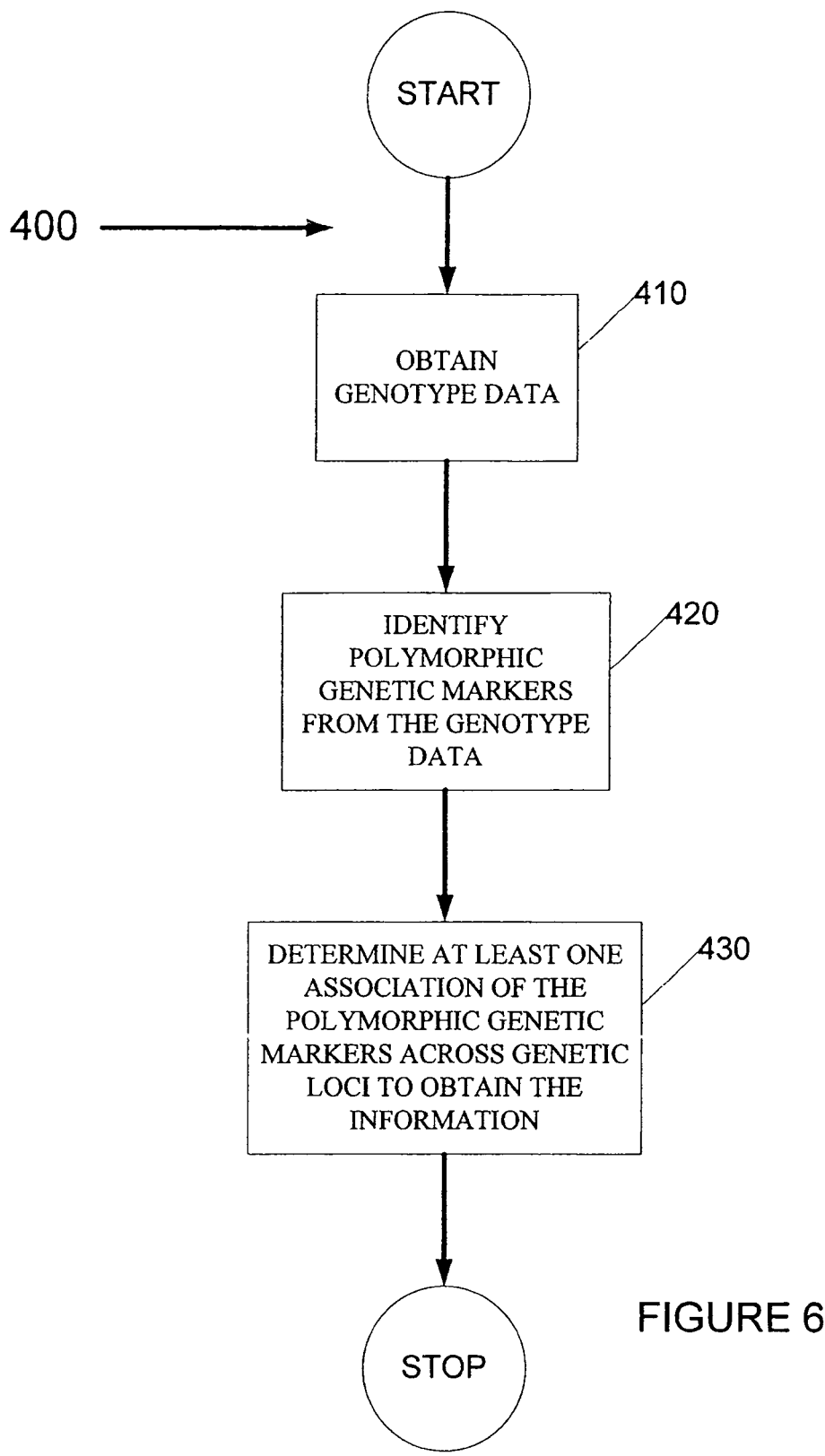
FIG. 6 shows a flow diagram of a top level of an exemplary embodiment of the method according to the present invention for establishing the haplotype of one or more genetic samples from genotype data obtained from the corresponding one or more genetic samples.

FIG. 6 shows a flow diagram of a top level of one exemplary embodiment of the method 400 according to the present invention for establishing the haplotype of one or more genetic samples from genotype data obtained from the corresponding one or more genetic samples. This method can be executed by the system 300 of FIG. 5, or by any other arrangement or system that is capable of implementing the method. For example, in step 410, the genotype data (associated with one or more genetic samples) is obtained. Then, in step 420, the polymorphic genetic markers are identified from the genotype data. Further, one or more associations of the polymorphic genetic markers across genetic loci are determined to obtain the information associated with the haplotype data.

While the invention has been described in connecting with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein. For example, the exemplary embodiments of the present invention can also be applicable for polyploid organisms, as well as diploid organisms. It should be understood that the present invention is operable on one or more chromosome of an organism, and can be used even if certain marker information is ambiguous or missing altogether. It is intended that the specification and the described examples are considered as exemplary only, with the true scope and spirit of the invention indicated by the following claims. Additionally, all references cited herein are hereby incorporated by this reference as though set forth fully herein.

What is claimed is:

1. A computer implemented process for determining restriction fragment length polymorphism (RFLP) haplotypes, comprising:
   a) receiving optical mapping data comprising ordered restriction maps of pieces of single DNA molecules of a single individual;
   b) identifying the RFLP markers from the received optical mapping data using an expectation maximization procedure;
   c) using a processor, computing data for phasing of neighboring pairs of RFLP markers using a maximum likelihood procedure; and
   d) determining the RFLP haplotypes using the computed data by combining RFLP markers into contiguous sets of loci (contigs) of phased RFLP markers.

2. The process of claim 1, further comprising at least one of outputting or storing the RFLP haplotypes of the ordered restriction map set in a storage arrangement.

3. The process of claim 1, further comprising computing a confidence measure for the phasing of the individual pairs of neighboring RFLP markers.

4. The process of claim 3, further comprising at least one of outputting or storing the confidence measure in a storage arrangement.

5. The process of claim 3, wherein a proportional relationship is provided between an amount of the received data and at least one of a number of RFLP markers detected, a resolution of the RFLP markers or the confidence measure.

6. The process of claim 1, further comprising determining a data sizing error and a quantity of the data, wherein the data sizing error and the quantity of the data received is determined so that at least one of the RFLP haplotypes substantially span a complete chromosome.

7. The process of claim 1, further comprising determining a minimum size of the maps in the ordered restriction map set and a level of coverage so that the haplotype phasing substantially spans the entire length of at least one chromosome.

8. The process of claim 1, wherein computing the data for phasing of individual pairs of neighboring heterozygous RFLPs is an approximately linear function of a total number of heterozygous RFLP markers.

9. A system for determining restriction fragment length polymorphism (RFLP) haplotypes, comprising:
a processor configured to:
   a) receive optical mapping data comprising ordered restriction maps of pieces of single DNA molecules of a single individual;
   b) identify the RFLP markers from the received optical mapping data using an expectation maximization procedure;
   c) compute data for phasing of neighboring pairs of the RFLP markers using a maximum likelihood procedure; and
   d) determine the RFLP haplotypes using the computed data by combining RFLP markers into contiguous sets of loci (contigs) of phased RFLP markers.

10. The system of claim 9, wherein the processing arrangement, when executed, is further configured to at least one of output or store the RFLP haplotypes in a storage arrangement.

11. The system of claim 9, wherein the processing arrangement, when executed, is further configured to compute a confidence measure for the phasing of the individual pairs of neighboring heterozygous RFLP markers.

12. The system of claim 11, wherein the processing arrangement, when executed, is further configured to at least one of output or store the confidence measure in a storage arrangement.

13. The system of claim 11, wherein a proportional relationship is provided between an amount of the received data and at least one of a number of RFLP markers detected, a resolution of the RFLP markers or the confidence measure.

14. The system of claim 9, wherein the processing arrangement, when executed, is further configured to determine a data sizing error and a quantity of the data, and wherein the data sizing error and the quantity of the data received is determined so that the corresponding RFLP haplotypes substantially span a complete chromosome.

15. The system of claim 9, wherein the processing arrangement, when executed, is further configured to determine a minimum size of the maps in the ordered restriction map set and a level of coverage so that the haplotype phasing substantially spans the entire length of at least one chromosome.

16. The system of claim 9, wherein the data for phasing of individual pairs of neighboring heterozygous RFLPs is an approximately linear function of a total number of heterozygous RFLP markers.

17. A non-transitory computer-accessible medium having stored thereon computer executable instructions for determining restriction fragment length polymorphism (RFLP) haplotypes of a diploid organism, which, when the executable instructions are executed by a processing arrangement, configure the processing arrangement to:
   a) receive optical mapping data comprising ordered restriction maps of pieces of single DNA molecules of a single individual;
   b) identify RFLP markers from the received optical mapping data using an expectation maximization procedure;
   c) compute data for phasing of neighboring pairs of the RFLP markers using a maximum likelihood procedure; and
   d) determine the RFLP haplotypes using the computed data by combining RFLP markers into contiguous sets of loci (contigs) of phased RFLP markers.

18. The computer-accessible medium of claim 17, wherein the processing arrangement is further configured, when executing the instructions, to at least one of output or store the RFLP haplotypes in a storage arrangement.

19. The computer-accessible medium of claim 17, wherein the processing arrangement is further configured, upon the execution of the instructions, to compute a confidence measure for the phasing of the individual pairs of neighboring heterozygous RFLP markers.

20. The computer-accessible medium of claim 19, wherein the processing arrangement is further configured, upon the execution of the instructions, to at least one of output or store the confidence measure in a storage arrangement.

21. The computer-accessible medium of claim 19, wherein a proportional relationship is provided between an amount of the received data and at least one of a number of RFLP markers detected, a resolution of the RFLP markers or the confidence measure.

22. The computer-accessible medium of claim 17, wherein the processing arrangement is further configured, upon the execution of the instructions, to determine a data sizing error and a quantity of the data, and wherein the data sizing error and the quantity of the data received is determined so that the corresponding RFLP haplotypes substantially span a complete chromosome.

23. The computer-accessible medium of claim 17, wherein the processing arrangement is further configured, upon the execution of the instructions, to determine a minimum size of the optical maps and a level of coverage density so that the haplotype phasing substantially spans the entire length of at least one chromosome.

24. The computer-accessible medium of claim 17, wherein the data for phasing of individual pairs of neighboring heterozygous RFLPs is an approximately linear function of a total number of heterozygous RFLP markers.

\* \* \* \* \*